United States Patent [19]

Sanderson et al.

[11] Patent Number: 5,587,164
[45] Date of Patent: Dec. 24, 1996

[54] PORCINE REPRODUCTIVE AND RESPIRATORY SYNDROME VIRUS ANTIGEN AND PROCESSES FOR THE PREPARATION AND USE OF SAID ANTIGEN IN VACCINES AND DIAGNOSTICS

[75] Inventors: Thomas Sanderson, Ames, Iowa; Michael J. McGinley, Lenexa, Kans.; Jeffrey J. Zimmerman, Ames, Iowa; Howard T. Hill, Cambridge, Iowa; Michael C. Meetz, Nevada, Iowa; Eugene C. Pirtle, Ames, Iowa; Sabrina L. Swenson, Madrid, Iowa; George P. Shibley, Leawood, Kans.

[73] Assignees: Bayer Corporation, Pittsburgh, Pa.; Iowa State University Research Foundation, Inc., Ames, Iowa

[21] Appl. No.: 349,865

[22] Filed: Dec. 6, 1994

Related U.S. Application Data

[63] Continuation of Ser. No. 14,915, Feb. 8, 1993, abandoned.

[51] Int. Cl.$^6$ .......................... A61K 39/00; A61K 39/38; A61K 39/12; A61K 39/193
[52] U.S. Cl. ..................... 424/218.1; 424/184.1; 424/815; 424/202.1; 435/235.1; 435/237
[58] Field of Search ................ 424/184.1, 202.1, 424/218.1, 815; 435/235.1, 237

[56] References Cited

U.S. PATENT DOCUMENTS 5,213,795  5/1993  Carlson et al. .......................... 424/89

FOREIGN PATENT DOCUMENTS

| 2076744 | 2/1993 | Canada. | |
|---|---|---|---|
| 2081638 | 4/1993 | Canada. | |
| 595436 | 5/1994 | European Pat. Off.. | |
| 9221375 | 12/1992 | WIPO | A61K 39/12 |
| 9303760 | 3/1993 | WIPO. | |
| 9306211 | 4/1993 | WIPO. | |
| 9307898 | 4/1993 | WIPO. | |

OTHER PUBLICATIONS

Wenovoort et al. 1991. Mystery Swine Disease in the Netherlands... Vet. Quarterly 13(3):121–130.
Pol et al. 1991. Pathological, Ultrastructured and Immunohisto chemical... Vet. Quarterly, 13(3):137–142.
Terpstra et al. 1991. Experimental Reproduction of Porcine ... Vet. Quarterly, 13(3:131–136.
Albina et al. 1992. An Enzyme Linked Immunosorbent ... Ann. Rech. Vet. 23:167–76.
Archives of Virology, vol. 133, No. 3–4, (Month Unavailable) 1993, N.Y., pp. 477–483 H. S. Kim et al, "Enhanced replication of porcine reproductive and respiratory syndrome (PRRS) virus in a homogeneous subpopulation of ma–104 cell line".
European Patent Application No. 92114469.7.
Procine Reproductive and Respiratory Syndrome (Mystery Swine Disease) Virus Infection in Growing Pigs–D. Smith et al.
J. Vet. Diagn invest 4:117–126 (1992)–James E. Collins et al.
J. Vet Diagn invest 4:134–138 (1992)–Wensvoort et al.
Am J. Vet Res. vol. 53, No. 4, Apr. 1992–pp. 485–488 W. T. Christianson et al.
J. Vet. Diagn Invest 4:127–133 (1992) David A. Benfield et al.
J. Vet Diagn Invest 4:139–143 (1992) Yoon et al.
J. Vet Diagn Invest 4:186–188 (1992)–Robert B. Morrison et al (pp. 186–187 Attached Only).
The Veterinary Quarterly, vol. 13, No. 3, Jul. 1991–G. Wensvoort et al–pp. 121–130, 135–143.
J. Vet Diagn Invest 4:144–147 (1992)–J Yoon et al.
International Pig Veterinary Society (Proceeding–I)–Aug. 17–20, 1993–108–134 (Abstract).
International Symposium on Swine Infertility & Respiratory Syndrome (SIRS, PRRS, PEARS) May 17–19, 1992 (Abstracts).
Conference of Research Workers in Animal Diseases–Nov. 9, 10, 1991 (Abstracts).
Procine reproductive and Respiratory Syndrome (Mystery Swine Disease) Virus Infection in Growing Pigs–D. Smith et al.
J. Vet Diagn invest 4:117–126 (1992)–James E. Collins et al.
J. Vet Diagn invest 4:134–138 (1992)–Wensvoort et al.
Am J. Vet Res, vol. 53, No. 4, Apr. 1992–pp. 485–488 W. T. Christianson et al.
J. Vet. Diagn Invest 4:127–133 (1992) David A. Benfield et al.
J. Vet Diagn Invest 4:139–143 (1992) Yoon et al.
J. Vet Diagn Invest 4:186–188 (1992)–Robert B. Morrison et al. (pp. 186–187 Attached Only).
The Veterinary Quarterly, vol. 13, No. 3, Jul. 1991–G. Wensvoort et al–pp. 121–130, 135–143.
J. Vet Diagn Invest 4:144–147 (1992)–J Yoon et al.
International Pig Veterinary Society (Proceeding–I)–Aug. 17–20, 1993–108–134–(Abstract).
International Symposium on Swine Infertility & Respiratory Syndrome (SIRS, PRRS, PEARS) May 17–19, 1992 (Abstracts).
Conference of Research Workers in Animal Diseases–Nov. 9, 10, 1991–(Abstracts).
Archives of Virology, vol. 133, No. 3–4, (Month Unavailable) 1993, N.Y., pp. 477–483, H. S. Kim, et al, "Enhanced replication of porcine reproductive and respiratory syndrome (PRRS) virus in homogeneous subpopulation of ma–104 cell line".

Primary Examiner—James C. Housel
Assistant Examiner—N. M. Minnifield
Attorney, Agent, or Firm—Joseph C. Gil; Godfried R. Akorli

[57] ABSTRACT

A process for growing a PRRSV in a tissue culture which is susceptible to infection to replicate the virus to an amount sufficient to protect animals against PRRS or be used in diagnosing PRRS or identifying the molecular structure of PRRSV for development of recombinant products, comprising inoculating the virus onto the tissue culture and harvesting the replicated virus.

3 Claims, No Drawings

PORCINE REPRODUCTIVE AND RESPIRATORY SYNDROME VIRUS ANTIGEN AND PROCESSES FOR THE PREPARATION AND USE OF SAID ANTIGEN IN VACCINES AND DIAGNOSTICS

This is a continuation of application Ser. No. 08/014,915, filed Feb. 8, 1993, now abandoned

BACKGROUND OF THE INVENTION

1. Field of the Invention

The present invention relates to a porcine reproductive and respiratory syndrome virus (PRRSV) isolate. More specifically, the present invention relates to diagnostic and protective antigens and vaccine for porcine reproductive and respiratory disease of pigs, and the methods of making and using the same.

2. Brief Description of the Prior Art

Porcine reproductive and respiratory syndrome is rapidly emerging as an economically devastating disease problem for U.S. and European swine producers. The syndrome was first described in the U.S. in 1987, with similar descriptions surfacing in Europe and Canada, two to three years later. The disease syndrome has been referred to by many different names including mystery swine disease, abortus blau, blue eared pig disease, porcine epidemic abortion and respiratory syndrome (PEARS), swine infertility and respiratory syndrome (SIRS). The name porcine reproductive and respiratory syndrome (PRRS) is employed hereinafter.

The etiological agent capable of reproducing the disease syndrome has been identified as a small enveloped spherical RNA virus, with an average virion diameter of 62 nm and a 25–30 nm core surrounded by an envelope. This virus has been tentatively grouped as a member of the genus Arterivirus within the Togaviridae family. The porcine reproductive and respiratory syndrome virus (PRRSV) isolate, described herein, fits this tentative classification and has been shown to reproduce the disease syndrome.

The disease syndrome associated with PRRSV is characterized by acute and chronic reproductive failure in adult female swine and severe to mild respiratory disease in young pigs. Reproductive failure is characterized by late term abortions resulting in increased incidence of mummified, stillborn and weak born pigs with markedly reduced chances for survival. Chronic problems with delayed return to estrus in infected sows has also been described. Respiratory disease sequela range from marked fever and interstitial pneumonitis to mild upper respiratory signs (i.e. sneezing, coughing, and nasal or ocular discharge) in young pigs. Recent (1990) serological and herd history studies indicate that at least 50% of U.S. swine herds have been exposed to PRRSV or have experienced reproductive failure and respiratory disease indicative of PRRSV infection.

Due to the recent emergence of this disease syndrome, studies on the pathogenesis, epidemiology and control of disease have been limited. As would be realized, an efficient propagation and processing of the antigens comprising PRRSV, will facilitate the development of a PRRSV vaccine as an aid in the prevention and control of porcine reproductive and respiratory syndrome.

SUMMARY OF THE INVENTION

In accordance with the foregoing, the present invention encompasses a virus isolate designated as ISU-P which is useful in the preparation of antigens for the diagnosis of porcine reproductive and respiratory syndrome and the induction of a protective immune response to porcine reproductive and respiratory syndrome virus (PRRSV). Also encompassed by the invention are the processes for making and using the antigens.

In a present embodiment of the invention, PRRSV isolate can be obtained by a process comprising isolating the PRRSV by co-cultivation of 10% weight/volume (w/v) lung homogenates from virus infected pigs with primary porcine alveolar macrophage or continuous cell line cultures at 35° C. The virus isolate designated as ISU-P has been deposited under the terms of the Budapest Treaty at the American Type Culture Collection, 12301 Parklawn Drive, Rockville, Md. 20852, U.S.A. on Mar. 16, 1993 under the accession number ATCC VR 2402.

The present invention further encompasses propagation of the virus to high titer in certain cell lines such as an African Green Monkey Kidney continuous cell line (MA 104) and a unique cloned derivative of the same (9009B). The cloned derivative of the continuous cell line designated as (9009B) has been deposited under the terms of the Budapest Treaty at the American Type Culture Collection, 12301 Parklawn Drive, Rockville, Md. 20852, U.S.A. on Mar. 16, 1993 under the accession number ATCC CRL 11302.

Also encompassed by the invention are processes for preparing and using live virus or killed virus antigens (conventional or recombinant) and the vaccines resulting therefrom by combining an immunologically effective amount of the virus with diluent and/or adjuvant, respectively.

It has been found that direct experimental immunization of sows with live virus or contact with live virus immunized sows prevented reproductive failure following an intranasal challenge with virulent PRRSV.

It has also been found that inactivated, adjuvanted PRRSV vaccines protected pigs from PRRS infection post challenge as measured by lack of virus replication in vaccinates as compared with non-vaccinated control pigs.

DETAILED DESCRIPTION OF THE INVENTION

As set forth above, the present invention is directed to the isolation of the PRRSV virus isolate ISU-P for the purpose of obtaining vital antigens for use in vaccines and diagnostic assays. The ISU-P isolate was obtained from the lung tissue of a weak born pig. Illustratively, a 10% w/v tissue homogenate from lung, spleen, and lymph node was prepared in Minimal Essential Media supplemented with antibiotics (MEM+A) to minimize the potential for contamination. The crude homogenate was clarified by centrifugation at 4° C. for 15 minutes at 1500×g. Clarified supernatant was diluted 1:5 in MEM+A and 1.0 mL was adsorbed onto a 48 hour old confluent monolayer of MA 104 cells or primary alveolar macrophages in 25 $cm^2$ flasks. Following a 2 hour adsorption period at 35° C. monolayers were washed twice with MEM+A, and 5.0 mL of MEM+A supplemented with 5.0% gamma-irradiated fetal calf serum was added. Virus isolation flasks were incubated at 35° C. in a 5% $CO_2$ atmosphere and observed daily for evidence of cytopathic effect (CPE). The PRRSV ISU-P cytopathic effect began with the rounding of small foci of 5 to 10 cells and progressed as many cells became pyknotic and detached from the substrate over the course of 4 to 7 days post infection.

The ISU-P isolate was confirmed as a PRRSV isolate by fluorescent antibody staining with PRRSV group specific monoclonal antibody, designated in the public domain as SDOW17. In addition, negative stained virus infected cells were examined by transmission electron microscopy for the presence of virus particles. The virus particles observed were spherical and enveloped with an average virion diameter of 65 nm and core diameter of 27 nm. Tissue culture virus characterized in this manner was used to experimentally reproduce late term abortion and reproductive failure in pregnant sows (Table 1). Table 1 shows that pregnant gilts exposed to either ISU-P-infected lung homogenates (PRRS-hm) or ISU-P grown in a cell culture (PRRS-tc) demonstrate typical disease signs of porcine reproductive and respiratory syndrome (PRRS). In the PRRS-hm groups there were no normal pigs farrowed. In the PRRS-tc groups only 4 of 33 pigs were farrowed normal. In comparison, 29 of 30 (96.7%) of the non-exposed pigs were normal at farrowing. The fact that ISU-P, even after purification in tissue culture, can reproduce the disease of PRRS confirms that this isolate is correctly classified as a member of the genus Arterivirus within the Togaviridae family. This isolate has also been found to produce a mild interstitial pneumonia in experimentally infected pigs.

It is a feature of the invention that the PRRSV in accordance with the invention can be grown in certain tissue culture cells which effectively replicate the virus to a level sufficient enough to provide the antigenic mass necessary to be incorporated in vaccines which can protect pigs and/or pregnant gilts or sows from PRRS challenge. Illustratively, the PRRSV can be grown in a tissue culture cell designated MA 104 by Whittaker BioProducts. Virus propagation experiments, employing identical culture conditions, with MA 104 cells obtained from three different sources indicate that a high degree of variability exists among MA 104 cells in terms of the ability to support PRRSV replication to high titer. One MA 104 cell culture designated MA 104(M) by Miles Inc., Agriculture Division, Animal Health Products Group, and used in the studies described herein, consistently supported PRRSV replication to high titer. Furthermore, a cell line clone, generated at Miles Inc., Agriculture Division, Animal Health Products Group, which derived from MA 104(M), designated 9009B, supports replication of PRRSV to titers higher than the parental cell line. Therefore, the preferred tissue culture cell for growth of ISU-P is 9009B. The following more fully illustrates cell culture propagation of the PRRSV ISU-P.

Tissue culture cells [MA 104 (M) and 9009B] were grown and maintained in Dulbecco's modified minimum essential media, high glucose (DMEM/HG), supplemented with 5% fetal calf serum and buffered with 1.3 g/L sodium bicarbonate. Cell passages were made with sufficient cell counts to attain a 80–100% confluent monolayer in 48 hours. PRRSV ISU-P virus stocks were diluted in DMEM/HG+5% fetal calf serum buffered to pH 6.8 with PIPES. Virus was inoculated onto the cell sheet at a low multiplicity of infection (MOI) and incubated at 36° C. Infected cultures were observed daily for CPE for 4–7 days. Infected cultures were harvested when 90–100% CPE was evident. Maximum virus antigenic mass was obtained after one –70° C. freeze/thaw cycle. Mean virus titers resulting from propagation in MA 104(M) cells ranged from $10^{3.0}$ to $10^{4.5}$ flourescent antibody infectious dose $_{50}$/ml (FAID $_{50}$/ml). Virus titers achieved by propagation in the 9009B cell clone ranges from $10^{5.5}$ to $10^{6.5}$ FAID $_{50}$/ml. Titers of this magnitude make it possible to incorporate sufficient antigenic mass into commercial scale PRRSV vaccine formulations of greater than 50L in volume.

As would be realized by those skilled in the art, once the PRRSV can be propagated to high levels of antigenic mass, derivatives of this virus including subunits thereof which are effective in accordance with the invention, can be obtained by means known to the art such as extraction from the virus. Additionally, the protective antigens can be identified at the molecular level and reproduced and expressed using recombinant technology.

Vital fluids for vaccine formulation were inactivated by two methods. The inactivants chosen were formalin and binary ethylenimine (BEI). Inactivation was performed by standard methods described more fully herein. Formalin inactivation was accomplished by mixing viral fluids with stock 37% formaldehyde to a final formalin concentration of 0.05%. The formalin-virus mixture was held at room temperature (approximately 25° C.) with constant mixing for 24 hours. Samples were taken at times 0, 8, 12 and 24 hours and assayed for live virus in 9009B cells. Cytopathic effect and fluorescent staining with group specific monoclonal antibody detected live PRRSV only at time=0 hours.

Inactivation with BEI was accomplished by combining stock 0.1M BEI (20.5 g/L 2-bromo-ethylamine HBR in 0.175N NaOH) with viral fluids to a final concentration of 1.0 mM BEI. Inactivation was performed by holding the BEI-virus mixture at room temperature with constant mixing for 48 hours. Virus inactivation was halted by the addition of 1.0M sodium thiosulfate to a final concentration of 0.1 mM with mixing for 2 hours. Samples were taken at times 0, 2, 4, 8, 12, 24 and 48 hours and assayed for live virus as described above. Live PRRSV was detected only at times=0, 2 and 4 hours.

In the preparation of a modified live or attenuated vaccine of the invention, the PRRSV is altered so that it can still infect the host in a limited manner but cannot cause signs of disease in the host. Normally, such alteration of the virus takes place by passaging it through a non-host cell such as African Green Monkey Kidney cells. Initially, the virus may not grow well or even not all. In the latter case, it may be necessary to force the virus to adapt to growth in cell culture. This can be done by adding the virus to the cell culture at a high or low multiplicity of infection (MOI). Alternately, the virus can be force-passaged or blind passaged along with the cells until enough cytopathic effect is observed, thus indicating that virus is being adapted. As adaptation occurs, the virus titer will increase as is observed when the PRRSV isolate ISU-P is passaged from the MA 104(M) cell line to the 9009B cell line. Table 1 shows that the tissue culture passaged PRRSV ISU-P (PRRS-tc) may be less virulent than that isolated from lung homogenates, a typical result of adaptation. Data disclosed in Table 2 indicate that the method of making vaccines in accordance with this invention are especially effective in conferring protection against PRRS.

The inactivated PRRSV ISU-P was adjuvanted as follows. Inactivated fluids were adjuvanted with adjuvants selected from the group consisting of Freund's complete adjuvant (FCA), Freund's incomplete adjuvant (FIA), a carbopol based adjuvant, and Diamond Scientific Adjuvant B (Adj B). These adjuvants represent the major types used in vaccine manufacture. Oil-based adjuvants are represented by FCA, FIA and ADJ B. Aqueous-based adjuvants are represented by carbopol. The inactivated PRRSV ISU-P may optionally contain a suitable preservative.

Vaccine formulations with FCA and FIA were prepared by emulsifying the inactivated virus, typically in equal volumes of inactivated virus fluid and adjuvant using an 18 guage double luer lock apparatus and two syringes. The fluids were expressed repeatedly through the assembly between syringes until a thickened semi-solid emulsion was formed. The emulsions were loaded directly into syringes for administration.

Vaccine formulations with Adj B were prepared by mixing stock Adj B with an equal volume of inactivated PRRSV ISU-P viral fluid. Adjuvant and virus was mixed by stirring at room temperature for 1 hour. Adjuvanted vaccine was aseptically transferred to sterile multidose vials and stored at 4° C. prior to administration.

Carbopol-based vaccine formulations were prepared by mixing stock carbopol adjuvant with inactivated viral fluids to a final adjuvant concentration of 10% v/v. Adjuvant and virus was mixed by stirring at room temperature for 4 hours. Adjuvanted vaccine was aseptically transferred to sterile multidose vials and stored at 4° C. prior to administration.

PRRSV ISU-P virus at a preinactivation titer as low as $10^{5.0}$ FAID$_{50}$/mL was used in the various vaccine formulations described.

In order to show that PRRSV isolate ISU-P could protect against porcine reproduction and respiratory syndrome, two vaccination/challenge studies were conducted. In the first study, 4 gilts were immunized with live PRRSV ISU-P by oronasal exposure to virus via either a direct route or contact with diseased pigs. Two gilts of the same age were left unimmunized (unexposed) and were housed separately to serve as controls. The direct-exposure vaccinates (#57 and #58) received 3.0 ml of virus inoculum intranasally. They seroconverted by 14 days post exposure according to an Indirect Fluorescent Antibody Test. The contact-exposed gilts (#476 and #480) were immunized by the oronasal route after being placed in close contact with diseased pigs. These pigs seroconverted by 90 days post exposure. Seroconversion is indicated by an IFA titer greater than 1:20.

After the immunized gilts seroconverted, their estrus was synchronized and they were bred. Pregnancy was confirmed by ultrasound. On gestation day 90, vaccinate and control pregnant gilts received 3.0 mL of PRRS challenge virus at a titer of $1\times10^4$ FAID$_{50}$, intranasally.

Control gilts #52 and #477 demonstrated early signs of disease in that they had reduced appetites and elevated body temperatures (103°–104° F.) for two to three days post challenge. No clinical signs of disease were noted in the ISU-P exposed (vaccinated) gilts. These results demonstrate protection from the clinical respiratory disease syndrome.

All gilts were held until pigs were weaned (4 weeks post farrowing). Table 2 shows the farrowing results from this experiment.

Farrowing results were recorded as to gestation length (gestation is normally shortened by PRRS infection), stillbirths or dead fetuses, weak pigs and mummies. These farrowing difficulties are all indicative of PRRS infection in pregnant gilts or sows. Additionally, the number of normal pigs were noted.

Neither of the control gilts farrowed normal pigs (0 of 22 pigs were normal). Seven (7) of 22 pigs were born dead and 15 of 22 were weak born pigs. The length of gestation of the control gilts was shortened by 2.5 days which is typical of PRRS in pregnant swine. In the immunized group (n=50) 40 pigs or 80% were born normal. Six (6) of 50 pigs were born dead and 4 of 50 fetuses appeared mummified at farrowing. There were no weak pigs in the vaccinate group. It is clear that gilts previously exposed to live PRRSV ISU-P which are bred and then challenged are protected from challenge as demonstrated by lack of direct clinical signs of disease in the gilts and by protection of the fetuses which they carry.

As would be realized, since the IFA test reagents which were used to determine the serostatus of the gilts in this study were derived from PRRSV ISU-P and since there is a direct correlation between the serostatus of the gilts and protection from PRRS, PRRSV ISU-P isolate can be useful in diagnostic tests such as Indirect Fluorescent Antibody tests as demonstrated herein, ELISAs, serum neutralization assays, Direct Fluoroescent Antibody assays and other art-known diagnostic assays. Hence, a diagnostic assay derived from antigen obtained from PRRSV ISU-P can be prepared and used in accordance with the invention.

In the second vaccination/challenge study, young pigs (4 to 6 weeks of age) were vaccinated with several inactivated, adjuvanted PRRSV ISU-P vaccines. A vaccine antigen pool was prepared by inactivation of the PRRSV ISU-P with BEI as described earlier and adjuvanted with either Carbopol, FCA/FIA or Adj B. A second vaccine antigen pool was prepared by inactivation of the PRRSV ISU-P with formalin as described earlier and adjuvanted with the same 3 adjuvants. Three mock vaccines were produced in order to make sure that the adjuvants and cells could not stimulate a false immunological response. Mock vaccines were prepared by adjuvanting uninfected tissue culture cells. Two pigs were vaccinated with each vaccine. Vaccines were administered subcutaneously on days 0, 21, 42 and 64. Seven days after the last vaccination the pigs were challenged intranasally with $10^{3.5}$ FAID$_{50}$ of virulent live PRRSV. All pigs were observed daily post challenge for clinical signs of disease. Additionally, blood samples were drawn and processed for recovery of virus in tissue culture. Live virus found in the blood stream post challenge signifies that a viremia has occurred.

Serum neutralization titers were evaluated at the beginning of the study, on the day of challenge and at 19 days post challenge. It should be noted that the serum neutralization test is less sensitive than the IFA test used in the previous study. Therefore, one cannot compare these titer results with the previous titer results.

Table 3 lists the results of the challenge. No clinical signs of disease were observed in vaccinated or control pigs. Additionally, neither vaccinates nor controls developed serum neutralization titers during the vaccination period. This indicates that there was no exposure to live virus during this time period (controls remained negative) and also indicates that the vaccines did not stimulate a humoral response high enough to be measured by a serum neutralization test. The fact that serum neutralization titer response post challenge was significant indicates that all pigs were effectively challenged with the live PRRS virus. A verification of this challenge exposure is the percentage of control pigs demonstrating viremia. All but one of the control pigs (87.5%) became infected. The immune response in vaccinated pigs was so strong that they were able to block viremia. Only 1 of 12 of the vaccinated pigs (8.3%) demonstrated viremia. Therefore, the vaccines protected 91.7% of the pigs.

Without being bound to any particular theory of the invention, it is believed that force-passaging of the original PRRSV isolate through a specially-adapted clone of MA104(M) African Green Monkey Cells (9009B) may have successfully altered one or more epitopes of the virus resulting in enhanced immunogenicity of this virus so as to allow production of vaccine in a field where other scientists have failed.

TABLE 1

Reproduction of late term abortion and reproduction failure in sows exposed to PRRSV isolate ISU-P as compared to non-exposed control sows.

| Sow # | Gestation Length(a) | Virus Preparation | Stillbirths | Weak | Mummies | Normal |
|---|---|---|---|---|---|---|
| I. PRRS Exposed Group | | | | | | |
| 57 | 112 days | PRRS-hm[b] | 6 | 8 | 0 | 0 |
| 54 | 108 days | PRRS-hm | 6 | 1 | 0 | 0 |
| 649 | 112 days | PRRS-hm | 3 | 7 | 0 | 0 |
| 58 | 112 days | PRRS-hm | 4 | 4 | 3 | 0 |
| 166 | 112 days | PRRS-tc[c] | 0 | 2 | 6 | 1 |
| 164 | 113 days | PRRS-tc[d] | 2 | 2 | 5 | 1 |
| 80 | 110 days | PRRS-tc[e] | 2 | 2 | 2 | 2 |
| Totals | | | 23 | 26 | 16 | 4 |
| II. Non-Exposed Control Group | | | | | | |
| 52 | 114 days | na | 0 | 0 | 0 | 11 |

TABLE 1-continued

Reproduction of late term abortion and reproduction failure in sows exposed to PRRSV isolate ISU-P as compared to non-exposed control sows.

| Sow # | Gestation Length(a) | Virus Preparation | Still-births | Weak | Mummies | Normal |
|---|---|---|---|---|---|---|
| 56 | 115 days | na | 0 | 0 | 0 | 12 |
| 163 | 116 days | na | 1 | 0 | 0 | 7 |
| Totals | | | 1 | 0 | 0 | 30 |

[a] Normal swine gestation period is 114
[b] PRRSV positive gnotobiotic pig lung homogenate inoculum
[c] Tissue culture derived PRRSV, $10^{3.0}$ Fluorescent antibody infectious dose 50 per ml (FAID 50/ml)
[d] tissue culture derived PRRSV, $10^{4.0}$ FAID 50/ml
[e] tissue culture derived PRRSV, $10^{5.0}$ FAID 50/ml

TABLE 2

Farrowing Results of ISU-P Immunized and Non-immunized Gilts

| GILT NO. | IFA TITER | GESTATION LENGTH | STILLBIRTHS OR DEAD | WEAK PIGS | MUMMIES | NORMAL |
|---|---|---|---|---|---|---|
| 57v | + | 113 days | 2* | 0 | 0 | 7 |
| 58V | + | 114 days | 4 | 0 | 3 | 11 |
| 476V | + | 113 days | 0 | 0 | 1 | 10 |
| 480V | + | 114 days | 0 | 0 | 0 | 12 |
| 52 C | − | 111 days | 5 | 7 | 0 | 0 |
| 477 | − | 112 days | 2 | 8 | 0 | 0 |
| TOTALS | | | 6 vacc. 7 cont. | 0 vacc. 15 cont. | 4 vacc. 0 cont. | 40 vacc. 0 cont. |

+ indicates an IFA titer of >20
− indicates an IFA titer of <20
V indicates vaccinates
C indicates controls

TABLE 3

PRRSV inactivated vaccine trial summary.

| | | Mean SN Each Challenge | Mean SN Post-Challenge[a] | Virus Isolation |
|---|---|---|---|---|
| Vaccine Group | | | | |
| BEI, PRRS-Carbopol | n = 2 | <1:2 | 1:82 | neg/neg |
| BEI, PRRS-FCA/FIA | n = 2 | <1:2 | 1:4 | neg/neg |
| BEI, PRRS-AdjB | n = 2 | <1:2 | 1:5 | neg/neg |
| Form., PRRS-Carbopol | n = 2 | <1:2 | 1:23 | neg/pos |
| Form., PRRS-FCA/FIA | n = 2 | <1:2 | 1:2 | neg/neg |
| Form., PRRS-AdjB | n = 2 | 1:3 | 1:8 | neg/neg |
| Mock Vaccine Group | | | | |
| Mock AG - carbopol | n = 2 | <1:2 | <1:2 | pos/pos |
| Mock AG - FCA/FIA | n = 2 | <1:2 | <1:2 | pos/pos |
| Mock AG - AdjB | n = 2 | <1:2 | <1:2 | pos/pos |

[a] SN response on day 19 post-challenge, termination of the experiment.
[b] Virus isolation from plasma at anytime during the 19 day post-challenge test period. Virus isolation detected by CPE in 9009B cells and confirmed by FA staining of the same with PRRSV group specific monoclonal antibody SD0W17.

What is claimed:

1. A vaccine prepared by the process of growing a porcine reproductive and respiratory syndrome virus (PRRSV) in a tissue which is susceptible to infection and replication of PRRSV to an amount sufficient to protect animals against PRRS comprising inoculating the PRRSV onto tissue cells and harvesting the replicated virus, releasing the virus from the tissue cells and adjusting the virus antigenic mass by dilution, concentration or extraction to produce an immunologically effective amount of the antigenic mass for a modified live or inactivated formulation of the vaccine wherein the PRRSV is an isolate designated as ISU-P and having an Accession number ATCC VR 2402.

2. A porcine reproductive and respiratory syndrome virus isolate designated as ISU-P and having an Accession number ATCC VR 2402.

3. A continuous cell line designated as 9009B and having an Accession Number ATCC CRL 11302.

* * * * *

UNITED STATES PATENT AND TRADEMARK OFFICE
Certificate

Patent No. 5,587,164                                                    Patented: December 24, 1996

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Thomas Sanderson, Libertyville, IL (US); Michael J. McGinley, Lenexa, KS (US); Jeffrey J. Zimmerman, Ames, IA (US); Howard T. Hill, Cambridge, IA (US); Michael C. Meetz, Nevada, IA (US); Eugene C. Pirtle, Ames, IA (US); Sabrina L. Swenson, Madrid, IA (US); George P. Shibley, Leawood, KS (US); and Kyoung-Jin Yoon, Ames, IA (US).

Signed and Sealed this Twenty-third Day of September 2008.

<div align="right">

LYNETTE R. F. SMITH
*Supervisory Patent Examiner*
Art Unit 1645

</div>